United States Patent
Cooker et al.

(10) Patent No.: US 6,281,369 B1
(45) Date of Patent: Aug. 28, 2001

(54) EPOXIDATION CATALYST AND PROCESS

(75) Inventors: Bernard Cooker, Malvern; Jennifer D. Jewson, Boyertown; Wilson H. Onimus, Holmes, all of PA (US)

(73) Assignee: Arco Chemical Technology, L.P., Greenville, DE (US)

( * ) Notice: Subject to any disclaimer, the term of this patent is extended or adjusted under 35 U.S.C. 154(b) by 0 days.

(21) Appl. No.: 09/731,565

(22) Filed: Dec. 7, 2000

(51) Int. Cl.[7] .................... C07D 301/06; C07D 301/08
(52) U.S. Cl. .............................. 549/533; 549/532
(58) Field of Search ..................... 549/533, 532

(56) References Cited

U.S. PATENT DOCUMENTS

| 5,646,314 | 7/1997 | Crocco et al. ................ 549/531 |
| 5,744,619 | 4/1998 | Nemeth et al. ................ 549/523 |
| 5,780,654 | 7/1998 | Nemeth et al. ................ 549/531 |
| 6,005,123 | 12/1999 | Dessau et al. ................ 549/531 |
| 6,008,388 | 12/1999 | Dessau et al. ................ 549/531 |

FOREIGN PATENT DOCUMENTS

| 1001038 | 6/1989 | (BE) . |
| 19600709 | 7/1997 | (DE) . |
| 4-352771 | 12/1992 | (JP) . |
| H8-269029 | 10/1996 | (JP) . |
| H8-269030 | 10/1996 | (JP) . |
| WO 96/02323 | 2/1996 | (WO) . |
| WO 97/25143 | 7/1997 | (WO) . |
| WO 97/31711 | 9/1997 | (WO) . |
| WO 97/47386 | 12/1997 | (WO) . |

*Primary Examiner*—Ba K. Trinh
(74) *Attorney, Agent, or Firm*—William C. Long

(57) ABSTRACT

The stability of a noble metal/titanium zeolite catalyst is improved by elevated temperature calcination with an oxygen containing gas; the catalyst is useful in epoxidation involving the reaction of olefin, oxygen and hydrogen.

6 Claims, No Drawings

EPOXIDATION CATALYST AND PROCESS

FIELD OF THE INVENTION

This invention relates to the preparation of a novel epoxidation catalyst comprised of a titanium zeolite catalyst which has been modified with a noble metal such as palladium, which catalyst has enhanced stability, and to the use of the catalyst for the production of oxirane compounds such as propylene oxide.

BACKGROUND OF THE INVENTION

Oxiranes constitute an important class of chemical intermediates useful for the preparation of polyether polyols, glycols, glycol ethers, surfactants, functional fluids, fuel additives and the like. Many different methods for synthesizing oxiranes from the corresponding olefins have been described in the literature. A Japanese patent application assigned to the Tosoh Corporation and published in 1992 (Kokai No. 4-352771) proposed making propylene oxide by reacting propylene, hydrogen and oxygen using a catalyst comprising a Group VIII metal and a crystalline titanosilicate. Improvements to or variations of this basic process were subsequently described in the following published patent applications: WO 97/25143, DE 19600709, WO 96/02323, WO 97/47386, WO 97/31711, JP H8-269030, JP H8-269029, U.S. Pat. Nos. 6,005,123, 6,008,388 and 5,646,314.

As with any chemical process, it would be desirable to attain still further improvements in epoxidation methods of this type. In particular, extending the useful life of the catalyst would significantly enhance the commercial potential of such methods. A problem has been that the noble metal tends to be leached or otherwise lost from the catalyst during use which results in loss of activity and selectivity. Additionally, loss of noble metal imposes an economic penalty which may render the process uneconomic.

SUMMARY OF THE INVENTION

The present invention provides a process for the preparation and use of a catalyst comprised of a titanium zeolite and a noble metal characterized in that the catalyst has improved stability and resistance to loss from the zeolite during use, and to the use of same in epoxidations.

DETAILED DESCRIPTION OF THE INVENTION

The catalysts of the present invention are comprised of a titanium zeolite and a noble metal (preferably an element of Group VIII of the Periodic Table). Suitable zeolites are those crystalline materials having a porous molecular sieve structure with titanium atoms substituted in the framework. The choice of zeolite employed will depend upon a number of factors, including the size and shape of the olefin to be epoxidized. For example, it is preferred to use a relatively small pore titanium zeolite such as a titanium silicalite if the olefin is a lower aliphatic olefin such as ethylene, propylene, or n-butene. Where the olefin is propylene, the use of a TS-1 titanium silicalite is especially advantageous. For a bulky olefin such as cyclohexene, a larger pore titanium zeolite such as a titanium zeolite having a structure isomorphous with zeolite beta may be preferred.

The titanium-containing zeolites useful as catalysts in the epoxidation step of the process comprise the class of zeolitic substances wherein titanium atoms are substituted for a portion of the silicon atoms in the lattice framework of a molecular sieve. Such substances are known in the art.

Particularly preferred titanium-containing zeolites include the class of molecular sieves commonly referred to as titanium silicalites, particularly "TS-1" (having an MFI topology analogous to that of the ZSM-5 aluminosilicate zeolites). "TS-2" (having an MEL topology analogous to that of the ZSM-11 aluminosilicate zeolites), and "TS-3" (as described in Belgian Pat. No. 1,001,038). Also suitable for use are the titanium-containing molecular sieves having framework structures isomorphous to zeolite beta, mordenite, ZSM-48, ZSM-12, and MCM-41. The titanium-containing zeolite preferably contains no elements other than titanium, silicon and oxygen in the lattice framework, although minor amounts of boron, iron, aluminum, and the like may be present. Other metals such as tin or vanadium may also be present in the lattice framework of the zeolite in addition to the titanium, as described in U.S. Pat. Nos. 5,780,654 and 5,744,619.

Preferred titanium-containing zeolite catalysts suitable for use in the process of this invention will generally have a composition corresponding to the following empirical formula $xTiO_2(1-x)SiO_2$ where x is between 0.0001 and 0.500. More preferably, the value of x is from 0.01 to 0.125. The molar ratio of Si:Ti in the lattice framework of the zeolite is advantageously from 9.5:1 to 99:1 (most preferably from 9.5:1 to 60:1). The use of relatively titanium-rich zeolites may also be desirable. The zeolite may or may not contain extra framework titanium.

As an essential aspect of the present invention, the catalyst comprises a noble metal supported on the above-described supports.

While any of the noble metals can be utilized (i.e., gold, silver, platinum, palladium, iridium, ruthenium, osmium), either alone or in combination, palladium is particularly desirable. Typically, the amount of noble metal present in the catalyst will be in the range of from 0.01 to 5 weight percent, preferably 0.05 to 2 weight percent. The manner in which the noble metal is incorporated into the catalyst is a critical feature of the invention.

The titanium silicalite used in the present invention is prepared by known procedures. An important feature is that the silicalite be subjected to an oxidative calcination as with air at elevated temperature, eg. 300 to 850° C., illustratively 550° C., in accordance with known procedures prior to use in accordance with the invention. The calcination is carried out until substantially complete removal of organic residues is accomplished. Thorough pre-washing and oxidative calcination procedures are described, for example in JP H-269029 and JP H-269030.

The titanium silicalite washing and calcination is carried out so as to remove essentially all of the residues of materials such as templating agents and the like used in the silicalite preparation, especially ammonium—type materials.

The calcined silicalite essentially free of residues is then treated as by ion exchange or impregnation procedures in order to incorporate the desired noble metal into the silicalite in appropriate amounts. Of the procedures, ion exchange is preferred with subsequent essentially complete removal of anionic residues from the resulting catalyst. Impregnation procedures can be used as is described herein later.

Removal of essentially all residues from the noble metal containing support is important and is conventionally accomplished by water washing and filtering techniques. Multiple washing and filtering steps are especially preferred. Preferably the noble metal/titanium silicalite catalyst is then dried by gentle heating, for example under vacuum.

A critical step in the preparation procedure is oxidative calcination of the noble metal/titanium silicate catalyst. Whereas prior art such as JP H8-269029 and JP H8-269030 teaches reduction of the noble metal/silicate catalyst, eg. 90° C. with a $H_2/N_2$ reducing gas, before use in epoxidation reactions, it has now been found that such prior catalysts are prone to rapid leaching of noble metal during epoxidation use thus severely limiting the practical utility of such catalysts.

It has now been found that the oxidation calcination of the noble metal/silicate catalyst results in the formation of a useful catalyst composition having greatly improved stability as against noble metal loss and thus greatly improved utility in the production of oxirane product such as propylene oxide.

The oxidative calcination is carried out at temperatures of at least 150° C. for illustratively 10 minutes to 24 hours. Calcination temperature in the range 150–650° C., preferably 250–600° C., and most preferably 300–550° C. are employed. The calcination gas is preferably air by reason of cost and availability although other mixtures of oxygen and inert gas can be used. Generally during the calcination it is advantageous to ramp the temperature up at the rate of 0.5–10° C., preferably 1–5° C./min to the desired upper temperature.

The above preparation markedly reduces noble metal loss during use of the catalyst in epoxidation reactions as will be demonstrated in experimental results herein after presented.

Additional improvements are also achieved where prior to or during epoxidation the catalyst is contacted with solutions buffered to slightly acid to basic pH. The preferred pH range is 5–8, preferably 6–7.5. See, for example, U.S. Pat. No. 5,646,314. Especially advantageous is the use of sodium and/or potassium salt buffered solutions. Excellent results are also achieved with calcium and magnesium salt containing solutions. Other Group I a and II a salts can be used as can compounds such as triphenyl phosphine. The combination of the calcination and contact with the buffered solution gives best results.

The olefin to be epoxidized can be any organic compound containing at least one site of ethylene unsaturation (i.e., at least one carbon-carbon double bond). The olefin can be aliphatic, aromatic or cycloaliphatic in character and may have either a linear or branched structure, with the site(s) of ethylenic unsaturation being terminal and/or internal. The olefin preferably contains 2–30 carbon atoms; the process of the invention is particularly suitable for epoxidizing $C_2-C_6$ mono-olefins. More than one double bond may be present, as in a diene or triene for example. The olefin may be a hydrocarbon (i.e., contain only carbon and hydrogen atoms) or may contain functional groups such as halide, carboxyl, hydroxyl, ether, carbonyl, cyano, or nitro, groups or the like.

Typical examples of suitable olefins include ethylene, propylene, 1-butene, cis- and trans-2-butene, 1,3-butadiene, pentenes, isoprene, hexenes, octenes, nonenes, decenes, undecenes, dodecenes, cyclopentene, cyclohexene, dicyclopentadiene, vinylcyclohexane, vinyl cyclohexene, allyl chloride, allyl alcohol, methallyl chloride, methallyl alcohol, alkyl acrylates and methacrylates, unsaturated fatty acids and esters thereof, styrene, -methylstyrene, divinylbenzene, indene and stilbene. Mixtures of olefins may, of course, be utilized if so desired. The process of this invention is especially useful for converting propylene to propylene oxide.

The process of the invention may be suitably conducted under the reaction conditions (e.g., temperature, pressure, reactant ratios) described in the following published patent applications: WO 96/02323, WO 97/25143, DE 19600709, WO 97/31711, WO 97/47386, JP 4-352771, JP H8-269029, and H8-269030.

The amount of catalyst used may be determined on the basis of the molar ratio of the titanium contained in the titanium zeolite to the olefin that is supplied per unit of time. Typically, sufficient catalyst is present to provide a titanium/olefin fed ratio of from 0.00001 to 0.1 per hour. The time required for the epoxidation may be determined on the basis of the gas hourly space velocity, i.e., the total volume of olefin, hydrogen, oxygen and carrier gas(es) per hour per unit of catalyst volume (abbreviated as GHSV). A GHSV in the range of 0.1 to 10,000 $hr^{-1}$ is typically satisfactory.

Depending on the olefin to be reacted, the epoxidation according to the invention can be carried out in the liquid phase, vapor phase, or in the supercritical phase. When a liquid reaction medium is used, as is preferred, the catalyst is preferably in the form of a suspension or as in fixed bed mode. The process may be performed using a continuous flow, semi-batch or batch mode of operation.

If epoxidation is carried out in the liquid phase, it is advantageous to work at a pressure of 1–100 bars and in the presence of one or more solvents. Suitable solvents include, but are not limited to, lower aliphatic alcohols such as methanol, ethanol, isopropanol, and tert-butanol, or mixtures thereof, and water. Fluorinated alcohols can be used. It is also possible to use mixtures of the cited alcohols with water. A mixture of water and methanol is preferred as solvent; hydrocarbons such as propane and/or propylene can be used as can carbon dioxide. Epoxidation according to the invention is carried out at a temperature effective to achieve the desired olefin epoxidation, preferably at temperatures in the range of 0–125° C. (more preferably, 20–80° C.). The molar ratio of hydrogen to oxygen can usually be varied in the range of $H_2:O_2=1:10$ to 5:1 and is especially favorable at 1:5 to 1:1. The molar ratio of oxygen to olefin can be 3:1 or more but preferably is 1:1 to 1:20, and most preferably 1:1.5 to 1:10. Relatively low $O_2$ to olefin molar ratios (e.g., 1:1 to 1:3) may be advantageous for certain olefins. As the carrier gas, any desired inert gas can be used. The molar ratio of olefin to carrier gas is then usually in the range of 50:1 to 1:50, and especially 20:1 to 1:1.

As the inert carrier gas, noble gases such as helium, neon, argon, krypton, and xenon are suitable in addition to nitrogen and carbon dioxide. Saturated hydrocarbons with 1–8, especially 1–6, and preferable with 1–4 carbon atoms, e.g., methane, ethane, propane, and n-butane, are also suitable. Nitrogen and saturated $C_1-C_4$ hydrocarbons are the preferred inert carrier gases. Mixtures of the listed inert carrier gases can also be used.

Specifically in the epoxidation of propylene according to the invention, propane can be supplied in such a way that, in the presence of an appropriate excess of carrier gas, the explosive limits of mixtures of propylene, propane, hydrogen, and oxygen are safely avoided and thus no explosive mixture can form in the reactor or in the feed and discharge lines.

EXAMPLES

As used herein, POE refers to propylene oxide and compounds derived from propylene oxide such as propylene glycol (PG), methoxy propanol, dipropylene glycol, tripropylene glycol, acetol, dipropylene glycol methyl ether, triproylene glycol methyl ether, and the like.

Selectivities are mols of product divided by the mols of reactant consumed multiplied by 100. Thus propylene based selectivity to POE (SPPOE) is the mols of POE divided by the mols of propylene consumed multiplied by 100. The hydrogen based selectivity to POE (SHPOE) is the mols of POE divided by the mols of hydrogen consumed multiplied by 100. The oxygen based selectivity to POE (SOPOE) is the mols of POE formed divided by the mols of oxygen consumed multiplied by 100.

Example 1

Catalyst A was made by ion exchanging Pd(II) from an aqueous solution of tetraamine palladium (II) chloride in excess ammonia on calcined TS-1, the TS-1 being added batchwise to the palladium solution. The mixture was agitated for 1 hour, filtered and the solid phase was washed with deionized water three times. The solid was dried at 50° C. in a vacuum oven, followed by calcination in air by ramping to 500° C. at 2° C/min and holding for 4 hours. The final catalyst had 0.45 wt % Pd and 2.01 wt % Ti.

1 gm of catalyst A was slurried in 100 cc of a pH buffer consisting of an aqueous solution of potassium dihydrogen phosphate and sodium hydroxide for 46.5 hrs at 60° C. and 1.5 psig with 1000 RPM stir bar agitation, 100 cc/min of gas feed with 9.96 vol % propylene, 3.73 vol % oxygen and 3.77 vol % hydrogen was fed. The mean POE rate was 0.00504 gmPO/gm cat hr, the mean propylene-based selectivity to POE was 68%, the mean oxygen-based selectivity to POE was 4% and the mean hydrogen-based selectivity to POE was 2%. The POE formed was 61% PO and 39% ring-open products, mainly PG. The liquid phase pH was 6.4 throughout. The Pd loss from the catalyst computed as –2.9% i.e. an apparent gain of 2.9%.

Example 2

Catalyst preparation B used Pd(II) trifluoroacetate in dilute aqueous solution, added continuously to a well-mixed aqueous slurry of air-calcined powdered 0.2 micron crystallite diameter TS-1 over 16 hours, the palladium(II) ions exchanging with the protons on the TS-1. The solid was filtered from the liquid and resuspended in deionized water and refiltered, three times. The material was dried under vacuum at 50° C. and calcined in air by ramping to 500° C. at 2° C./min and holding for 4 hours. The catalyst was then slurried in an aqueous solution of monosodium dihydrogen phosphate for 24 hours, filtered, resuspended in fresh deionized water and filtered. It was then dried at 50° C. under vacuum. The final catalyst was 0.1365 wt % Pd and 1.525 wt % Ti.

1 gm of catalyst B was run semi-continuously by slurrying in 100 cc of deionized water for 46.5 hours at 60° C. and 1.5 psig with 1000 RPM stir bar agitation, 100 cc/min of gas feed with 3.16 vol % propylene, 3.54 vol % oxygen and 4.14 vol % hydrogen. The mean POE rate was 0.0080 gmPO/gm cat hr, the mean propylene-based selectivity to POE was 99%, the mean oxygen-based selectivity to POE was 45% and the mean hydrogen-based selectivity to POE was 28%. The POE formed was 21% PO and 79% ring-open products, almost exclusively PG. The liquid phase pH fell from 5.23 to 3.22 during the run. The Pd loss from the catalyst computed as –7.7% i.e. an apparent gain of 7.7%.

Example 3

Catalyst C was made by ion exchanging Pd(II) from an aqueous solution of tetraamine palladium (II) dinitrate in excess ammonia to calcined TS-1, the TS-1 being added batchwise to the palladium solution. The mixture was agitated for 24 hours at 80° C., filtered, and the solid phase was washed with deionized water three times. The solid was dried at 60° C. in a vacuum oven, followed by calcined in air by ramping to 500° C. at 2° C./min and holding for 4 hours. The final catalyst had 0.19 wt % Pd and 0.89 wt % Ti.

0.5 gm of catalyst C was run semi-continuously by slurring in 100 cc of a pH buffer consisting of an aqueous solution of 0.1M potassium dihydrogen phosphate and 0.1M potassium hydroxide for 1 hour at 60° C. and 1.5 psig with 1000 RPM stir bar agitation, 100 cc/min of gas feed with 10 vol % oxygen and 4.0 vol % hydrogen. The mean POE rate was 0.0032 gmPOE/gm cat hr, the mean propylene-based selectivity to POE was 24%, the mean oxygen-based selectivity to POE was 2% and the mean hydrogen-based selectivity to POE was 1%. The POE formed was 58% PO and 42% ring-open products, mainly PG. The liquid phase pH was 6.4 throughout. The Pd loss from the catalyst computed as –8.1% i.e. an apparent gain of 8.1%.

Example 4

0.5 gm of catalyst C was run semi-continuously by slurrying in 100 cc of a pH buffer consisting of an aqueous solution of 0.01M potassium dihydrogen phosphate and 0.01M potassium hydroxide for 99 hours at 60° C. and 1.5 psig with 1000 RPM stir bar agitation, 100 cc/min of gas feed with 10 vol % propylene, 4.0 vol % oxygen and 4.0 vol % hydrogen. The mean POE rate was 0.0030 gmPOE/gm cat hr, the mean propylene-based selectivity to POE was 82.3%, the mean oxygen-based selectivity to POE was 4% and the mean hydrogen-based selectivity to POE was 3%. The POE formed was 77% PO and 28% ring-open products, mainly PG. The liquid phase pH was 6.7 throughout. The Pd loss from the catalyst computed as –8.1% i.e. an apparent gain of 8.1%.

Example 5 (Comparative)

Catalyst E was made by using an impregnation technique to add Pd(II) from an aqueous solution of tetraamine palladium (II) dinitrate in excess ammonia to calcined TS-1, the TS-1 being added batchwise to the palladium solution. The mixture was agitated for 24 hours at 80° C. and rotovaped. The solid was dried at 60° C. in a vacuum oven, followed by heating in $N_2$ by ramping to 150° C. at 2° C./min and holding for 4 hours. The final catalyst had 0.5 wt % Pd and 0.92 wt % Ti.

1.0 gm of catalyst E was run semi-continuously by slurrying in 100 cc of distilled water for 105 hours at 60° C. and 1.5 psig with 1000 RPM stir bar agitation, 100 cc/min of gas feed with 10 vol % propylene 4.0 vol % hydrogen. The mean POE rate was 0.0174 gmPOE/gm cat hr, the mean propylene-based selectivity to POE was 88%, the mean oxygen-based selectivity to POE was 27% and the mean hydrogen-based selectivity to POE was 15%. The POE formed was 32% PO and 68% ring-open products, mainly PG. The liquid phase pH was 5.2 throughout. The Pd loss from the catalyst computed as 58.8%.

Example 6 (Comparative)

Catalyst F was made by impregnation of aqueous Pd(II) tetraamine dinitrate in excess ammonia onto calcined TS-1, the TS-1 being batchwise added to the palladium solution. It was heated to 80° C. for 16 hours and then the water was stripped under vacuum at 50° C. and then the solid was dried at 60° C. under vacuum for 24 hours. The catalyst was then heated to 150° C. for 4 hours in flowing nitrogen. The final catalyst had 0.55 wt % Pd and 2.1 wt % Ti.

0.5 gm of catalyst F was run semi-continuously by slurrying in 100 cc of water for 54 hours at 60° C. and 3 psig, with 1000 RPM stir bar agitation, 100 cc/min of gas feed with 9.80 vol % propylene, 3.87 vol % oxygen and 4.21 vol % hydrogen. The solution pH fell to 4.08 at the close of the run. The mean POE rate was 0.0405 gm PO/gm cat hr, the mean propylene-based selectivity to POE (SPPOE) was 96%, the mean oxygen-based selectivity to POE (SOPOE) was 49% and the mean hydrogen-based selectivity to POE (SHPOE) was 26%. The POE was 66% and 34% ring-open products, mainly PG. The Pd loss from the catalyst was measured as 63%.

Example 7

Catalyst G was made by ion exchanging Pd(II) from an aqueous solution of tetraamine palladium (II) dinitrate in excess ammonia to calcined TS-1, the TS-1 being added batchwise to the palladium solution. The mixture was agitated for 24 hours to 80° C., filtered and the solid phase was washed with deionized water three times. The solid was dried at 60° C. in a vacuum oven, followed by calcination in air by ramping to 500° C. at 2° C./min and holding for 4 hours. The final catalyst had 0.53 wt % Pd and 0.91 wt % Ti.

1.0 gm of catalyst G was run semi-continuously by slurrying in 100 cc of distilled water for 125 hours at 60° C. and 1.5 psig with 1000 RPM stir bar agitation, 100 cc/min of gas feed with 10 vol % propylene, 4.0 vol % oxygen and 4.0 vol % hydrogen. The mean POE rate was 0.0041 gmPOE/gm cat hr, the mean propylene-based selectivity to POE was 54 %, the mean oxygen-based selectivity to POE was 4% and the mean hydrogen-based selectivity to POE was 2%. The POE formed was 2% PO and 98% ring-open products, mainly PG. The liquid phase pH was 3.5 throughout. The Pd loss from the catalyst computed as 17%.

Example 8

Catalyst H was made by ion exchanging Pd(II) from an aqueous solution of tetraamine palladium (II) dinitrate in excess ammonia to calcined TS-1, the TS-1 being added batchwise to the palladium solution. The mixture was agitated for 24 hours at 80° C., filtered and the solid phase was washed with deionized water three times. The solid was dried at 60° C. in a vacuum oven, followed by calcination in air by ramping to 500° C. at 2° C./min and holding for 4 hours. The final catalyst had 0.32 wt % Pd and 0.90 wt % Ti.

0.5 gm of catalyst H was run semi-continuously by slurrying in 100 cc of distilled water for 99 hours at 60° C. and 1.5 psig with 1000 RPM stir bar agitation, 100 cc/min of gas feed with 10 vol % propylene, 4.0 vol % oxygen and 4.0 vol % hydrogen. The mean POE rate was 0.0105 gmPOE/gm cat hr, the mean propylene-based selectivity to POE was 65%, the mean oxygen-based selectivity to POE was 6% and the mean hydrogen-based selectivity to POE was 3%. The POE formed was 5% PO and 95% ring-open products, mainly PG. The liquid phase pH was 3.8 throughout. The Pd loss from the catalyst computed as 22%.

Example 9

0.5 gm of catalyst C was run semi-continuously by slurrying in 100 cc of distilled water for 126 hours at 60° C. and 1.5 psig with 1000 RPM stir bar agitation, 100 cc/min of gas feed with 10% vol propylene, 4.0 vol % oxygen and 4.0 vol % hydrogen. The mean POE rate was 0.0063 gmPOE/gm cat hr, the mean propylene-based selectivity to POE was 88%, the mean oxygen based selectivity to POE was 6% and the mean hydrogen-based selectivity to POE was 3%. The POE formed was 7% PO and 92% ring-open products, mainly PG. The liquid phase pH was 4.0 throughout. The Pd loss from the catalyst computed as 21%.

Example 10

3 gm of catalyst D were run semi-continuously by slurrying in 100 cc of water for 93 hours at 60° C. and 3 psig with 1000 RPM stir bar agitation, 100 cc/min of gas feed with 9.86 vol % propylene, 3.77 vol % oxygen and 4.38 vol % hydrogen. The solution pH fell from 5.88 to 2.71 during the run. The mean POE rate was 0.0011 gm PO/gm cat hr, the mean propylene-based selectivity to POE (SPPOE) was 6%, the mean oxygen-based selectivity to POE (SOPOE) was 2% and the mean hydrogen-based selectivity to POE (SHPOE) was 1%. The POE was 29% PO and 71% ring-open products, mainly PG. The Pd loss from the catalyst was measured as 8.4%.

Example 11 (Comparative)

1.0 gm of catalyst G was run semi-continuously by slurrying in 100 cc of distilled water for 138 hours at 60° C. and 1.5 psig with 1000 RPM stir bar agitation, 100 cc/min of gas feed with 10 vol % propylene, 4.0 vol % oxygen and 4.0 vol % hydrogen. The mean POE rate was 0.0090 gmPOE/gm cat hr, the mean propylene-based selectivity to POE was 88%, the mean oxygen-based selectivity to POE was 40% and the mean hydrogen-based selectivity to POE was 45%. The POE formed was 37% PO and 63% ring-open products, mainly PG. The liquid phase pH was 5.8 throughout. The Pd loss from the catalyst computed as 68%.

Example 12 (Comparative)

Catalyst D was made by ion exchanging Pd(II) ions from an aqueous solution of tetraamine palladium (II) chloride in excess ammonia to calcined TS-1, the TS-1 being batchwise added to the palladium solution. The mixture was agitated for 1 hour, filtered and the solid phase was washed with deionized water three times. The solid was dried at 50° C. in a vacuum oven. The final catalyst had 0.49 wt % Pd and 1.86 wt % Ti.

1.5 gm of catalyst D were run semi-continuously by slurrying in 100 cc of water for 46.5 hours at 60° C. and 3 psig, with 1000 RPM stir bar agitation, 100 cc/min of gas feed with 9.17 vol % propylene, 3.93 vol % oxygen and 3.91 vol % hydrogen. The reactor solution pH fell from 8.07 to 4.05 during the run. The mean POE rate was 0.0185 gm PO/gm cat hr the mean propylene-based selectivity to POE (SPPOE) was 92%, the mean oxygen-based selectivity to POE (SOPOE) was 44% and the mean hydrogen-based selectivity to POE (SHPOE) was 27%. The POE was 41% PO and 59% ring-open products, mainly PG. The Pd loss from the catalyst was measured as 60%.

Example 13

Catalyst I was made by impregnation of aqueous Pd(II) tetraamine dinitrate in excess ammonia onto calcined evacuated TS-1, the TS-1 being batchwise added to the palladium solution. It was heated to 80° C. for 16 hours and then the water was stripped under vacuum at 50° C. and then the solid was dried at 60° C. under vacuum for 24 hours. The catalyst was then heated to 150° C. for 4 hours in flowing nitrogen and then the material was calcined in air by ramping to 500° C. at 2° C./min and holding for 4 hours. The final catalyst had 0.60 wt % Pd and 1.96 wt % Ti.

3 gm catalyst I were run semi-continuously by slurrying in 100 cc of water for 46.5 hours at 60° C. and 3 psig, with 1000 RPM stir bar agitation, 100 cc/min of gas feed with 10.1 vol % propylene, 3.9 vol % oxygen and 4.9 vol % hydrogen. The solution pH fell from 5.29 to 3.71 during the run. The mean POE rate was 0.0335 gm PO/gm cat hr, the mean propylene-based selectivity to POE (SPPOE) was 67%, the mean oxygen-based selectivity to POE (SOPOE) was 20% and the mean hydrogen-based selectivity to POE (SHPOE) was 9%. The POE was 3% PO and 97% ring-open products, mainly PG. The Pd loss from the catalyst was measured as 12%.

Example 14 (Comparative)

1.0 gm of catalyst E was run semi-continuously by slurrying in 100 cc of a pH buffer consisting of an aqueous solution of 0.1M potassium dehydrogen phosphate and 0.1M potassium hydroxide for 1 hour at 60° C. and 1.5 psig with 1000 RPM stir bar agitation, 100 cc/min of gas feed with 10 vol % propylene, 4.0 vol % oxygen and 4.0 vol % hydrogen. The mean POE rate was 0.0052 gmPOE/gm cat hr, the mean propylene-based selectivity to POE was 94%, the mean oxygen-based selectivity to POE was 6% and the mean hydrogen-based selectivity to POE was 3%. The POE formed was 80% PO and 20% ring-open products, mainly PG. The liquid phase pH was 6.7 throughout. The Pd loss from the catalyst computed as 13.7%.

Example 15 (Comparative)

0.5 gm of catalyst F was run semi-continuously by slurrying in 100 cc of a pH buffer consisting of an aqueous solution of potassium dihydrogen phosphate and sodium hydroxide for 70.5 hours at 60° C. and 3 psig, with 1000 RPM stir bar agitation, 100 cc/min of gas feed with 9.57 vol % propylene, 3.77 vol % oxygen and 3.74 vol % hydrogen. The solution pH was 6.5 throughout. The mean POE rate was 0.026 gm PO/gm cat hr, the mean propylene-based selectivity to POE (SPPOE) was 95%, the mean oxygen-base selectivity to POE (SOPOE) was 21% and the mean hydrogen-based selectivity to POE (SHPOE) was 12%. The POE was 84% PO and 16% ring-open products, mainly PG. The Pd loss from the catalyst was measured as 4.8%.

Example 16 (Comparative)

0.5 gm of catalyst F was run semi-continuously by slurrying in 100 cc of a pH buffer consisting of an aqueous solution of potassium dihydrogen phosphate and sodium hydroxide for 54 hours at 60° C. and 3 psig, with 1000 RPM stir bar agitation, 100 cc/min of gas feed with 8.84 vol % propylene, 3.84 vol % oxygen and 4.05 vol % hydrogen. The solution pH was 5.5 throughout. The mean POE rate was 0.022 gm PO/gmn cat hr, the mean oxygen-based selectivity to POE (SPPOE) was 94%, the mean oxygen-based selectivity to POE (SOPOE) was 14% and the mean hydrogen-based selectivity to POE (SHPOE) was 6%. The POE was 79% PO and 21% ring-open products, mainly PG. The Pd loss from the catalyst was measured as 15%.

Examples 1–4 demonstrate the outstanding stability of catalysts prepared in accordance with most preferred practice of the invention where the buffered epoxidation solution was used in conjunction the catalyst preparation.

Comparative Examples 5, 6, 11 and 12 demonstrate the high rate of noble metal loss from catalysts not prepared by the invention and used in non-buffered epoxidation solution.

Examples 7, shows use of catalysts prepared in accordance with the invention and used in non-buffered epoxidation solution. Results are better than those of Examples 5, 6, 11 and 12 but inferior to those of Examples 1–4.

Comparative Examples 14, 15, and 16 illustrate that catalysts not prepared in accordance with the invention have a higher loss of noble metal even in buffered epoxidation solution as compared to similar runs with catalysts prepared by the invention.

We claim:

1. In a process for the production of an oxirane compound by contacting an olefin, oxygen and hydrogen with a noble metal on titanium zeolite catalyst at epoxidation conditions, the improvement wherein the said catalyst is prepared by calcination in an oxygen containing atmosphere at temperatures above 150° C.

2. The process of claim 1 wherein the calcination is at a temperature of 250–600° C.

3. The process of claim 1 wherein the calcination is at a temperature of 300–500° C.

4. The process of claim 1 wherein the olefin is propylene.

5. The process of claim 1 wherein the noble metal is palladium.

6. The process of claim 1 wherein the epoxidation is carried out in the liquid phase at a slightly acidic to basic pH.

* * * * *